US006498005B1

(12) United States Patent
Nikiforov et al.

(10) Patent No.: US 6,498,005 B1
(45) Date of Patent: Dec. 24, 2002

(54) HOMOGENEOUS ASSAY METHODS

(75) Inventors: Theo T. Nikiforov, San Jose, CA (US); Sang Jeong, San Francisco, CA (US)

(73) Assignee: Caliper Technologies Corp., Mountain View, CA (US)

( * ) Notice: Subject to any disclaimer, the term of this patent is extended or adjusted under 35 U.S.C. 154(b) by 0 days.

(21) Appl. No.: 09/408,884

(22) Filed: Sep. 29, 1999

Related U.S. Application Data (60) Provisional application No. 60/102,486, filed on Sep. 30, 1998.

(51) Int. Cl.$^7$ .................................................. C12Q 1/68
(52) U.S. Cl. .................... 435/4; 435/5; 435/6; 435/7.5; 435/7.72; 435/7.91; 435/91.1; 435/91.2; 435/DIG. 4; 435/DIG. 15; 436/171; 436/172
(58) Field of Search ........................... 435/5, 4–6, 7.5, 435/7.72, 7.91, 91.1, 91.2, DIG. 4, DIG. 15; 436/171, 172

(56) References Cited

U.S. PATENT DOCUMENTS

| | | | |
|---|---|---|---|
| 5,223,409 | A | 6/1993 | Ladner et al. |
| 5,403,484 | A | 4/1995 | Ladner et al. |
| 5,779,868 | A | 7/1998 | Parce et al. |
| 5,858,195 | A | 1/1999 | Ramsey |
| 5,942,443 | A | 8/1999 | Parce et al. |
| 6,203,994 | B1 * | 3/2001 | Epps et al. .................. 435/7.1 |

FOREIGN PATENT DOCUMENTS

| | | |
|---|---|---|
| WO | WO98/46438 | 10/1998 |
| WO | WO98/49546 | 11/1998 |
| WO | WO99/64840 | 12/1999 |

OTHER PUBLICATIONS

Braunwalder, A.F. et al., "A Solid–Phase Assay for the Determination of Protein Tyrosine Kinase Activity of c–src Using Scintillating Microtitration Plates," *Anal. Biochem.* (1996) 234:23–26.

Braunwalder, A.F. et al., "Measurement of the Protein Tyrosine Kinase Activity of c–src Using Time–Resolved Fluorometry of Europium Chelates," *Anal. Biochem.* (1996) 238:159–164.

Casnellie, J.E., "Assay of Protein Kinases Using Peptides with Basic Residues for Phosphocellulose Binding," *Methods Enzymol.* (1991) 200:115–120.

Chijiwa, T. et al., Inhibition of Forskolin–induced Neurite Outgrowth and Proteing Phosphorylation by a Newly Synthesized Selective Inhibitor of Cyclic AMP–dependent Protein Kinase, N–[2–(p–Bromocinnamylamino)ethyl]–5–isoquinolinesulfonamide (H–89), of PC12D Pheochromocytoma Cells, *J. Biol. Chem.* (1990) 265(9):5267–5272.

Cohen, C.B. et al., "A Microchip–Based Enzyme Assay for Protein Kinase A" *Anal. Chem.* (1999) 273:89–97.

Facemyer, K.C. et al., "A New Method to Specifically Label Thiophosphorylatable Proteins with Extrinsic Probes. Labeling of Serine–19 of the Regulatory Light Chain of Smooth Muscle Myosin," *Bioconjugate Chem.* (1992) 3:408–413.

Hodges, R.R. et al., "'Post–Assay' Covalent Labeling of Phosphorothioate–Containing Nucleic Acids with Multiple Fluorescent Markers," *Biochemistry* (1989) 28:261–267.

Levine, L.M. et al., "Measurement of Specific Protease Activity Utilizing Fluorescence Polarization," *Anal. Biochem.* (1997) 247:83–88.

Pan, P. et al., "Caged Cysteine and Thiophosphoryl Peptides," *FEBS Letts* (1997) 405:81–85.

Seethala, R. et al., "A Homogeneous Fluorescence Polarization Assay for Src–Family Tyrosine Kinases," *Anal. Biochem.* (1997) 253:210–218.

Seethala, R. et al., "Fluorescence Polarization Competition Immunoassay for Tyrosine Kinases," *Anal. Biochem.* (1998) 255:257–262.

Witt, J.J. et al., "Rapid Protein Kinase Assay Using Phosphocellulose–Paper Absorption," *Anal. Biochem.* (1975) 66:253–258.

* cited by examiner

*Primary Examiner*—Bennett Celsa
(74) *Attorney, Agent, or Firm*—Matthew B. Murphy; Andrew L. Filler (57) ABSTRACT

The present invention provides a method of assaying an enzyme-mediated coupling reaction between a first and a second reactant. The method includes contacting the first reactant with the second reactant in the presence of the enzyme. The second reactant includes a thiol derivative to yield a first product including a thiol derivative. The thiol derivative is then detected in the first product.

18 Claims, 7 Drawing Sheets

SEQUENCE LISTING

<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence:Kinase
      substrate

<400> SEQUENCE: 1

Leu Arg Arg Ala Ser Leu Gly
 1               5

HOMOGENEOUS ASSAY METHODS

CROSS-REFERENCE TO RELATED APPLICATIONS

This application claims priority to Provisional U.S. patent application Ser. No. 60/102,486, filed Sep. 30, 1998, which is incorporated herein by reference in its entirety for all purposes.

BACKGROUND OF THE INVENTION

Protein tyrosine and serine/threonine kinases are an important class of enzymes involved in the regulation of a number of biological processes. These enzymes are an increasingly significant target for new drug design. Methods for the rapid, high-throughput screening of chemical libraries for the identification of new inhibitory structures against these enzymes are actively being pursued.

Traditionally, the enzyme activity of protein tyrosine and serine/threonine kinases has been assayed by following the transfer of a radioactive phosphate group from $\gamma^{32}P$ ATP to the tyrosine, serine or threonine residue of a suitable protein or peptide substrate (See, e.g., Witt, J. J. and Roskoski, R., Jr. (1975) *Anal. Biochem.* 66, 253–258 and Casnellie, J. E. (1991) *Methods Enzymol.* 200, 115–120). Following the phosphorylation reaction, the labeled product has to be separated from excess labeled ATP. This approach requires the use of radioactivity, involves multiple steps and is poorly suited for high-throughput screening applications. The scintillation proximity based approach represents an improvement, but it still has all the disadvantages of radioactive assays.

Several non-radioactive kinase assay approaches have been described that rely on the use of anti-phosphotyrosine antibodies. In the method of Braunwalder et al. (See, e.g., Braunwalder, A. F., Yarwood, D. R., Sills, M. A., and Lipson, K. E. *Anal. Biochem.* (1996) 238, 159–164), these antibodies are labeled with an Eu chelate. The substrate is immobilized to the surface of an ELISA plate, and the product of phosphorylation is detected using time-resolved fluorescence following incubation with the labeled antibodies. The main disadvantage of this method is its heterogeneous nature, which does not easily permit the detailed enzymological characterization of the kinase. As an alternative, a completely homogeneous approach has been described, where the binding of the anti-phosphotyrosine antibodies to the reaction product is detected by fluorescence polarization (See, e.g., Seethala, R. and Menzel, R. *Anal. Biochem.* (1997) 253, 210–218, and Seethala, R. and Menzel, R. *Anal. Biochem.* (1998) 255, 257–262). These methods may not work as well for serine/threonine kinase due to the lack of similar, high-affinity anti-phosphoserine/threonine antibodies.

Kinases can also assayed by separating the substrate from the phosphorylated product. This is generally done by a number of different methods, such as HPLC; capillary electrophoresis, TLC, ion-exchange chromatography etc. However, the need for an additional separation step represents a complication for high throughput screening applications.

It would generally be desirable to provide alternative approaches to assaying kinases as well as other enzymes having similar complications, which methods are adaptable to high-throughput screening methods. The present invention meets these and other needs.

SUMMARY OF THE INVENTION

In a first aspect, the present invention provides a method of assaying an enzyme-mediated coupling reaction between a first and a second reactant. The method comprises contacting the first reactant with the second reactant in the presence of the enzyme. The second reactant comprises a thiol derivative to yield a first product comprising a thiol derivative. The thiol derivative is then detected in the first product.

Another aspect of the present invention is a method of identifying a phosphorylatable substrate for a kinase enzyme. The method provides a phage display peptide library wherein each peptide in the library comprises a conserved phosphorylatable amino acid residue. The phage display library reacts with the kinase and ATPγS and contacted with a biotinylated haloacetate. Any biotinylated phage is immobilized on a solid support. DNA from any phage immobilized on the solid support is isolated and sequenced. A phosphorylatable peptide sequence is determined from a sequence of the DNA isolated from the phage.

DETAILED DESCRIPTION OF THE INVENTION

I. General Description of Assay Methods
A. General Assay Chemistries

The present invention provides novel methods for assaying a number of different reaction types that would normally require the use of heterogeneous assay formats, but through the use of a novel homogeneous assay format. In particularly preferred aspects, the methods of the present invention typically employ novel assay chemistries that yield reaction products that are independently detectable over and above the reactants used in the reaction, where previously described assays required heterogeneous formats, e.g., reaction followed by separation.

Generally, the present invention uses novel assay chemistries to permit the selective attachment of labeling group to either the product of the reaction of interest or one of the reactants involved in the reaction. In a heterogeneous format, a simple label group may be used which is selectively attached to one of the reactants or the product. The reactants and product are then separated and separately detected. The amount of product produced or substrate used is then determined by virtue of increases or decreases in the amount of label in either the product or reactants, respectively.

In order to provide a homogeneous assay format where the entire reaction mixture is maintained in the same reaction zone or vessel, however, use of a simple labeling group does not suffice, as there is typically no basis for identifying that the detected label originates from product, reactant, or otherwise unincorporated label. In the present invention therefore, the detectable moiety provides a basis for determining where the label originates, and thereby quantitating the amount of either the reactant or the product before or after the reaction of interest.

In preferred aspects of the present invention, the detectable label includes, in part, a large molecular weight moiety that is selectively attached to one of either the substrate or the product, but not the other. When attached to a reactant or the product that otherwise bears a fluorescent label, the large molecular weight compound yields a change in the level of polarized fluorescence emitted from the label over that of the reactant or product that is not attached to the large molecular weight moiety. In accordance with the present invention, assay chemistries are provided that facilitate the attachment of the large molecular weight compound to either one of the reactants, or the product.

Figure 1:
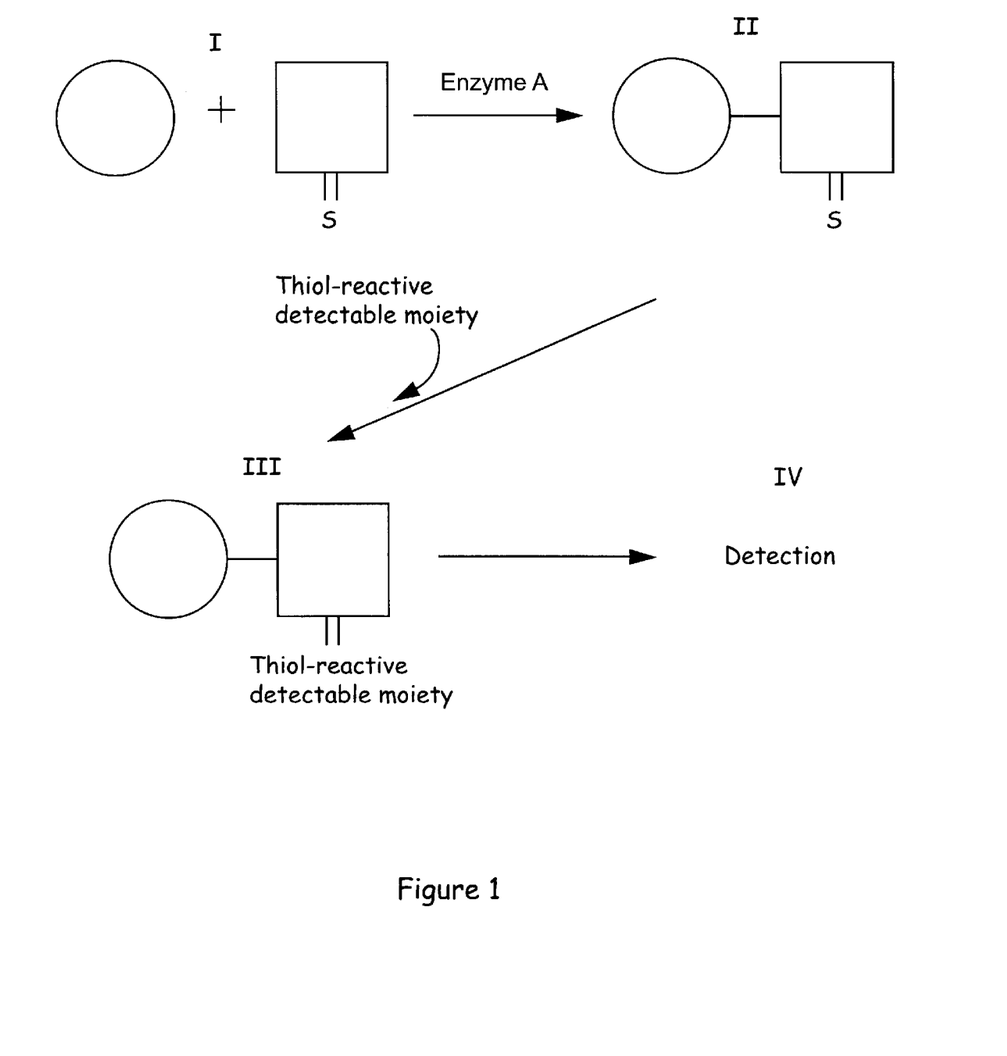
FIG. 1 is a schematic illustration of the process of the assay methods of the invention.

For example, in a first aspect, the present invention provides methods of assaying for the enzyme-mediated coupling of reactants, by providing one of the reactants as a thiol derivative, which yields a product bearing the thiol derivative. Once coupled, a further thiol-reactive derivative reactant bearing a detectable moiety is reacted and coupled to the thiol derivative to provide the labeled moiety on the coupled reactants. The detectable moiety is then detected and compared to a control to provide a relative level of activity of the enzyme that mediated the initial reaction. A schematic illustration of the general reaction is illustrated in FIG. 1. As shown, a first reactant (circle) is combined with a second reactant (square) that bears a reactive thiol, in the presence of the enzyme that is being assayed (Enzyme A) (I) to yield a product that bears the reactive thiol (II). This first product bearing the thiol derivative is then coupled with a thiol-reactive derivative that bears a detectable moiety (III), which reacts with the thiol group to couple the detectable moiety to the first product, yielding a second, detectable product. This detectable product is then detected (IV). In some cases, the reaction of interest already involves a thiol derivative as one of the reactants, e.g., glutathione-S-transferase mediated reactions.

B. Detection Schemes

As described above, a detectable moiety is attached to the product of the enzyme mediated reaction, either through a second reaction, or as a result of the enzyme mediated reaction. As used herein, the term detectable moiety is defined as a property of the ultimately detected product or compound that is distinguished and distinguishable from any of the preceding reactants or products in the overall process. For example, as noted above, in preferred aspects, fluorescence polarization is used as the detection scheme. In these schemes, a fluorescent reactant is generally incorporated into a product (which is also fluorescent) which then is detected based upon a change in its fluorescent polarization. As such, the mere presence of a fluorescent group does not provide a detectable moiety that distinguishes product from reactant. Instead, in this case, the detectable moiety would be the compound added to the reactant to provide its distinguishable fluorescence polarization. This is typically a large molecular weight compound, such as a protein (i.e., streptavidin), polypeptide (i.e., polylysine), nucleic acid, or the like. Alternatively, the detectable moiety is optionally a group or compound which allows easy attachment of a large molecular weight moiety to the product. For example, biotin is often used as a detectable moiety in that it is readily bound by streptavidin which can be detected either through an incorporated label, or by virtue of the change in size it imparts to the biotinylated product (yielding a consequent change in fluorescence polarization levels).

Of course, fluorescent moieties can be the detectable moiety as used herein, where the fluorescent moiety provides a different fluorescent signal when incorporated into the product as compared to the signal in the reactant. Examples of such fluorescent moieties optionally include, e.g., FRET dyes, donor-quencher pairs, etc. which produce different fluorescent signals when maintained in close proximity, e.g., both present in different reactants versus both being unified in a single product.

As noted above, in certain preferred aspects, fluorescence polarization change is used as a basis for detecting the progress of the reaction that is being assayed, e.g., measuring the coupling of a first fluorescent reactant to a second reactant. Measurement of differential polarization of free and bound ligands has long been utilized to determine relative ligand binding levels, and even to screen for compounds or conditions that might affect that binding. To date, such assays have been carried out in a contained fluid system, e.g., a cuvette or multiwell plate, where the components of the binding reaction, e.g., a labeled ligand and its receptor, are mixed in the presence or absence of a compound to be tested.

The principles behind the use of fluorescence polarization measurements as a method of measuring binding or coupling among different molecules are relatively straight-forward. Briefly, when a fluorescent molecule is excited with a polarized light source, the molecule will emit fluorescent light in a fixed plane, e.g., the emitted light is also polarized, provided that the molecule is fixed in space. However, because the molecule is typically rotating and tumbling in space, the plane in which the fluoresced light is emitted varies with the rotation of the molecule. Restated, the emitted fluorescence is generally depolarized. The faster the molecule rotates in solution, the more depolarized it is. Conversely, the slower the molecule rotates in solution, the less depolarized, or the more polarized it is. The polarization value (P) for a given molecule is proportional to the molecule's "rotational relaxation time," or the amount of time it takes the molecule to rotate through an angle of 68.5°. The smaller the rotational correlation time, the faster the molecule rotates, and the less polarization will be observed. The larger the rotational correlation time, the slower the molecule rotates, and the more polarization will be observed. Rotational relaxation time is related to viscosity ($\eta$), absolute temperature (T), molecular volume (V), and the gas constant (R). The rotational relaxation time is generally calculated according to the following formula:

$$\text{Rotational Relaxation Time}=3\eta V/RT$$

As can be seen from the above equation, if temperature and viscosity are maintained constant, then the rotational relaxation time, and therefore, the polarization value, is directly related to the molecular volume. Accordingly, the larger the molecule, the higher its fluorescent polarization value, and conversely, the smaller the molecule, the smaller its fluorescent polarization value.

In the performance of fluorescent binding assays, a typically small, fluorescently labeled molecule, e.g., a ligand, antigen, etc., having a relatively fast rotational correlation time, is used to bind to a much larger molecule, e.g., a receptor protein, antibody, protein conjugate, polypeptide, etc., which has a much slower rotational correlation time. The binding or coupling of the small labeled molecule to the larger molecule significantly increases the rotational correlation time (decreases the amount of rotation) of the labeled species, namely the labeled complex over that of the free unbound labeled molecule. This has a corresponding effect on the level of polarization that is detectable. Specifically, the labeled complex presents much higher fluorescence polarization than the unbound, labeled molecule.

Generally, the fluorescence polarization level is calculated using the following formula:

$$P=[I(\|)-I(\perp)]/[I(\|)+I(\perp)]$$

Where $I(\|)$ is the fluorescence detected in the plane parallel to the excitation light, and $I(\perp)$ is the fluorescence detected in the plane perpendicular to the excitation light.

In performing screening assays, e.g., for potential inhibitors, enhancers, agonists or antagonists of the binding or coupling function in question, the change in fluorescence polarization of bound versus free labeled ligand is compared in the presence and absence of different compounds, to determine whether these different compounds have any effect on the binding function of interest. In particular, in the presence of inhibitors of the binding function, the fluorescence polarization will decrease, as more free, labeled ligand is present in the assay. Conversely, enhancers of the binding function will result in an increase in the fluorescent polarization, as more complex and less free-labeled ligand are present in the assay.

II. Exemplary Kinase Assays

In at least a first aspect, the methods of the present invention provide an alternative approach for detecting kinase activity. These methods are readily adaptable to both low and high throughput kinase assays, e.g., screening of chemical libraries. The methods of the invention are also advantageous in that they do not require the use of radioactivity or antibodies and allow flexibility in the detection scheme.

Figure 2:
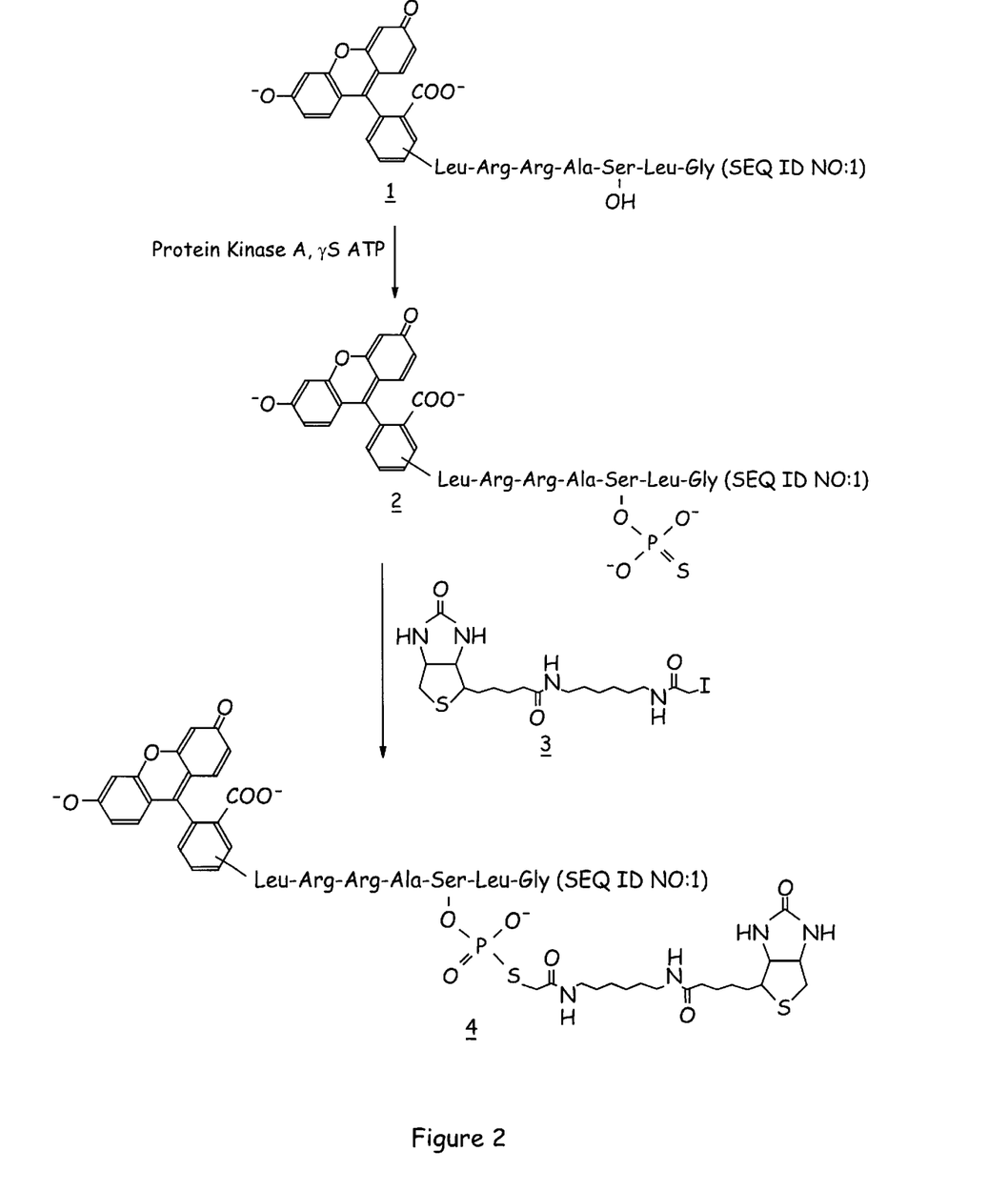
FIG. 2 illustrates the progress of a typical kinase reaction using the methods of the present invention.

The general scheme of the methods of the invention as applied to kinases is shown in FIG. 2 using protein kinase A ("PKA") and a fluorescent substrate as an exemplary system. However, it will be appreciated that a wide range of kinases may be assayed using the methods described herein. In assaying for kinase activity, the methods of the present invention take advantage of two factors. First, a nucleophilic sulfur of thiophosphates is generally reactive towards haloacetates. See, e.g., Facemyer, K. C. and Cremo, C. R. (1992) *Bioconjugate Chem.* 3, 408–413; Pan, P. and Bayley, H. (1997) *FEBS Letters* 405, 81–85; and Hodges, R. R., Conway, N. E., and McLaughlin, L. W. (1989) *Biochemistry* 28, 261–267. Second, a large number of protein kinases (both tyrosine and serine/threonine) accept the nonphysiological substrate γS-ATP as a replacement of its normal counterpart adenosine triphosphate. See, e.g., Facemyer, K. C. and Cremo, supra. With respect to kinase assays, the present invention takes advantage of these properties in a non-radioactive method for the detection of kinase activity. As a further advantage, the methods described herein are readily practiced in homogeneous phase and are easily automated for the purposes of high throughput screening of chemical libraries.

As shown in FIG. 2, in the first step of the method, a fluorescein labeled PKA substrate 1, known as Kemptide, is phosphorylated using γS-ATP instead of regular ATP, resulting in the generation of the thiophosphorylated product 2. The reaction mixture is then contacted with a solution of a thiol-reactive derivative of a detectable moiety. As shown, the thiol-reactive detectable moiety is an iodoacetyl derivative of biotin 3. In the instance shown, the reaction proceeds at room temperature.

The sulfur group of the thiophosphate derivative 2 reacts with the iodoacetyl function of 3 and leads to the formation of the biotinylated, fluoresceinated product 4. The formation of this product can be assessed in several ways. In order to develop a completely homogeneous assay, fluorescence polarization was selected as the analytical tool. However, a number of other detection schemes are also useful in conjunction with the assay methods described herein, including both heterogeneous formats and homogeneous formats. In the case of heterogeneous formats, it will be appreciated that the final reaction mixture following the thiophosphorylation and biotinylation reaction could be transferred to a streptavidin-coated microtiter plate and the biotinylated species (3, 4, and the product of reaction between 3 and γS-ATP) allowed to bind to the solid phase. Following a wash step, the fluorescent signal due to bound 4 can be detected using a fluorescence plate reader. The observed signal will be directly proportional to the concentration of 4, with no interference from the unmodified substrate 1. Second, the starting peptide substrate could be biotinylated and, following the thiophosphorylation, reacted with a haloacetyl derivative of a fluorescent dye. The mixture could then be captured onto a streptavidin coated plate. In the case of homogeneous assay formats, the reaction incorporates homogeneously detectable labeling moieties, e.g., fluorescent resonant energy transfer (FRET) dye-based formats, fluorescent donor-quencher pair based formats, and the like.

In the method shown, streptavidin was added to the reaction mixture and allowed to bind to all biotinylated species in the reaction mixture, including compound 4. Binding of streptavidin to 4 results in an increased fluorescence polarization value of product 4 compared to the substrate 1.

In screening applications, the above-described phosphorylation reaction is carried out in the presence of a compound or potential pharmaceutical candidate, which is being screened for an effect on the activity of the kinase reaction, e.g., as an inhibitor or enhancer of that activity. Where the screened compound is a kinase inhibitor it will result in a final fluorescence polarization value that is lower than that for the control in the absence of inhibitor or enhancer, while an enhancer will result in an increase in the final fluorescence polarization value relative to the control.

Although shown in FIG. 2 and described with reference to particular reaction steps, it will be appreciated that a number of variations are readily practicable in the context of the presently described methods. For example, rather than carrying out the two-step procedure described above, which requires the treatment of the thiophosphate with iodoacetyl-LC-biotin and streptavidin, it will be appreciated that single step procedures can also be used. For example, the thiophosphorylated product can optionally be treated directly with a thiol reactive derivative that is ultimately detectable. In the case of fluorescence polarization detection schemes, this is typically a large molecular weight species, e.g., a protein polypeptide, nucleic acid or the like, such as a bromoacetylated polylysine derivative or thiol-reactive streptavidin derivative. This would lead directly to the formation of a the detectable complex with the product, e.g., a high molecular weight complex of the product which would have a high fluorescence polarization value relative to the substrate alone. Further, and as noted above, these methods could readily be adapted to heterogeneous formats.

The methods described above are generally utilized in assaying relative activities of enzymes, e.g., in screening for potential effectors of those activities. However, the methods described above are also useful in identification of new compositions, and particularly substrate materials for the coupling reactions that are being assayed, e.g., phosphorylatable peptides, and the like. In particular, in the case of the kinase assay method described above, ATPγS, a particular kinase of interest, and a biotin-LC-iodoacetamide are used to interrogate a phage display peptide library that is constructed so as to have conserved therein a phosphorylatable residue (e.g., ser, thr, tyr). Phage display peptide libraries have been described in, e.g., U.S. Pat. Nos. 5,223,409 and 5,403,484, each of which is incorporated herein by reference. Those phage that display an appropriate peptide substrate for the particular kinase will be tagged with the γS phosphate group. Those tagged peptides are then biotinylated using the biotin-LC-iodoacetamide chemistry described above. The phage that bore these peptides are then isolated on streptavidin bearing solid supports, e.g., beads, and the encoding DNA is isolated. The DNA may then be sequenced to identify the peptide sequence or sequences that served as a substrate for the kinase. Alternatively, if necessary, the cycle can be repeated, inserting the isolated DNA into a further phage display library, to further enrich for the most optimized substrate, e.g., phosphorylatable peptide.

III. Exemplary Glutathione Assay

As with the kinase assay described above, the assay methods described here operate through the addition of a group or moiety that can be exploited in the detection of the product. In particular, a first reactant bears a fluorescent moiety. It is reacted with a second reactant that bears an appropriate coupling group, so as to yield a product that includes the fluorescent group and the coupling group. An additional detectable moiety, e.g., a large molecular weight compound, a quencher or FRET pair member for the fluorescent group on the first reactant, or the like, is then coupled to the coupling group to yield a product that is distinguishable from the first reactant. In particularly preferred aspects, the second detectable moiety comprises a large molecular weight group, and the product is distinguishable from the first reactant by virtue of a change in the level of polarized fluorescence emitted from the reaction mixture. In typical aspects, this is accomplished by providing the second reactant as a biotinylated reactant where the biotin forms the coupling group and avidin or streptavidin are used as the large molecular weight moieties.

Figure 3:
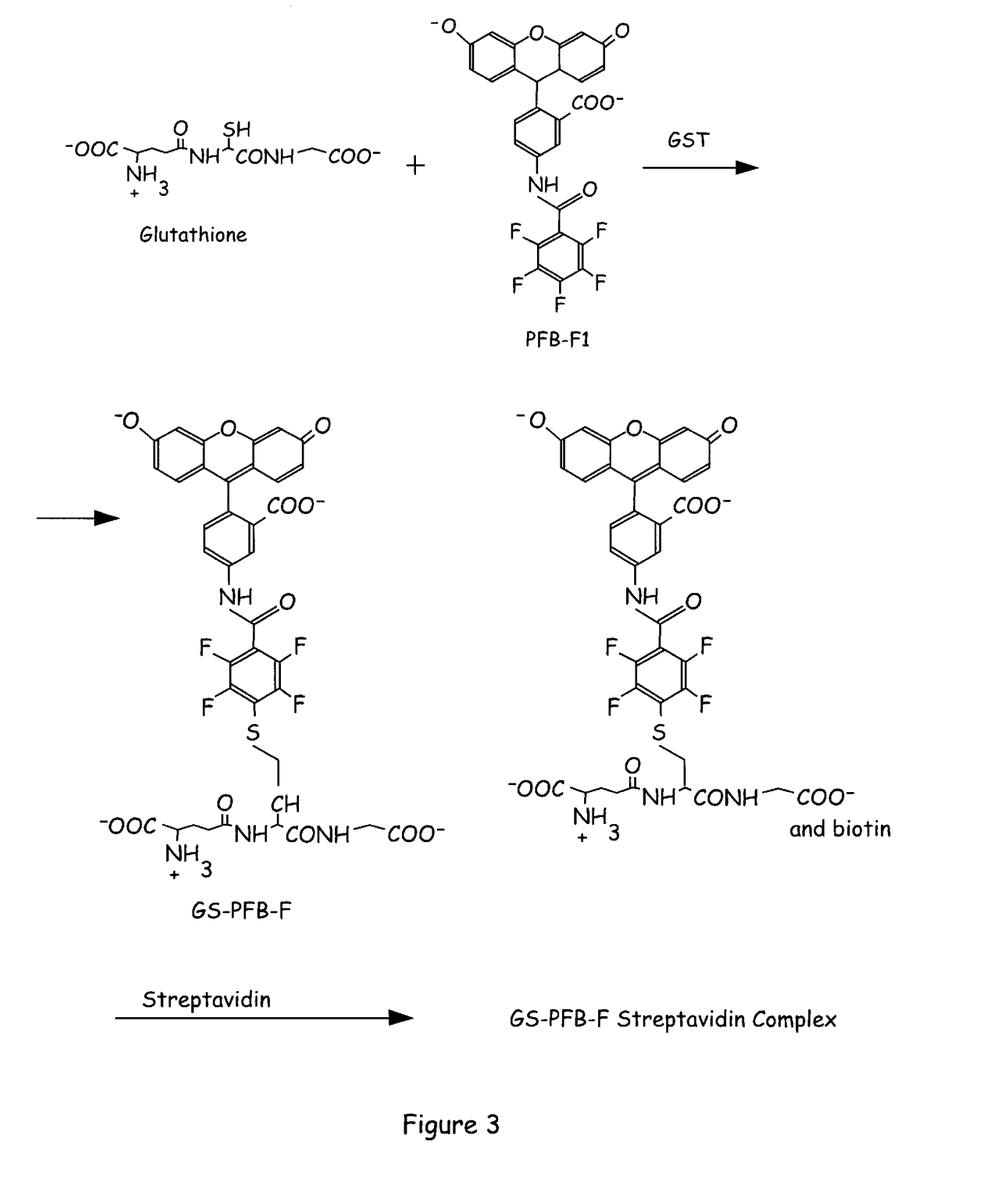
FIG. 3 illustrates the progress of an alternate assay method of the present invention for assaying glutathione-S-transferase activity.

This is illustrated in FIG. 3 in a method for assaying glutathione-S-transferase ("GST"). As shown, glutathione bearing one portion of the detectable moiety, e.g., biotin, is reacted with a fluorescent derivative substrate, e.g., PFB-F 1, in the presence of glutathione, to form a fluorescent biotinylated product. The biotinylated product is then coupled, via the biotin, to a large molecular weight molecule, e.g., avidin or streptavidin. Typically, assaying the reaction would require the separation of the fluorescent substrate from the product in order to ascertain the amount of fluorescent signal from the product. However, due to the presence of the streptavidin, the product and substrate will have markedly different rotational correlation times, allowing their differentiation using fluorescence polarization detection methods.

IV. Assay Systems

The present invention also provides assay systems that are useful in practicing the methods described herein. In its simplest form, the assay system comprises an assay receptacle in which the assayed reaction is carried out, and a detector for detecting the results of that reaction. In preferred aspects, the assay receptacle is selected from a test tube, a well in a multiwell plate, or other similar reaction vessel. In such cases, the various reagents are introduced into the receptacle and typically assayed right in the receptacle using an appropriate detection system, e.g., a fluorescence polarization detector.

Alternatively, and equally preferred is where the reaction receptacle comprises a fluidic channel, and preferably, a microfluidic channel. As used herein, the term microfluidic refers to a channel or other conduit that has at least one cross-sectional dimension in the range of from about 1 μm to about 500 μm. Examples of microfluidic devices useful for practicing the methods described herein include, e.g., those described in e.g., U.S. Pat. Nos. 5,942,443, 5,779,868, and International Patent Application No. WO 98/46438, the disclosures of which are incorporated herein by reference.

Figure 7:
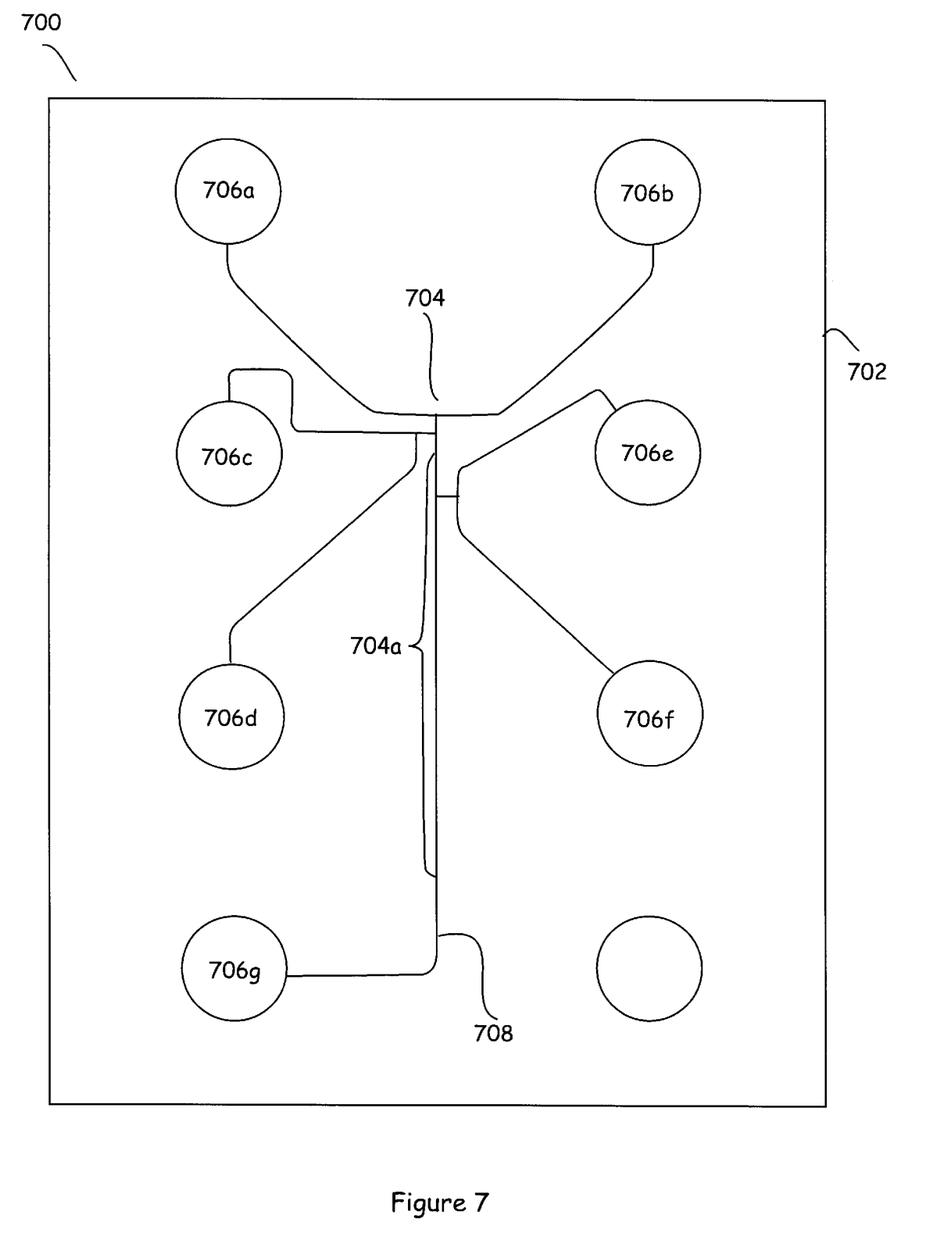
FIG. 7 illustrates an example of a microfluidic device useful in carrying out the methods of the present invention.

One example of a microfluidic device for carrying out the methods of the present invention is shown in FIG. 7. As shown, the microfluidic device 700 has a planar body structure 702 with a channel network 704 disposed within its interior. At each of the unintersected termini of the various channel segments is disposed a reservoir or well, e.g., well 706a. These reservoirs are used as ports for introducing reagents, buffers, samples and the like, into the channels 704 of the device 700.

The above-described devices and systems may generally be used to assay reagents for their ability to carry out the desired reaction, e.g., a coupling reaction, in order to determine, e.g., enzyme activity, concentration, or the like. However, in certain aspects, the systems are used in conjunction with a model reagent system to screen for compounds and/or conditions that are capable of affecting the underlying reaction. In particular, in accordance with the above described methods, an enzyme mediated coupling reaction between a first and second reactant is carried out in the channels of a microfluidic device. Specifically, the first reactant is contacted with the second thiol-derivative reactant in the presence of the enzyme in question within a reaction channel portion or zone of the device, e.g., channel segment 704a. The first and second reactants are delivered to the reaction zone 704a from their respective reservoirs, e.g., reservoirs 706a and 706c. Optionally, these reagents may be diluted by simultaneously delivering an appropriate amount of diluent from diluent wells 706b and 706d, respectively. The product of this reaction comprises a thiol derivative and is detected within a detection portion of the channel network, e.g., at detection window 708. The reaction is then carried out in the presence of a test compound that is transported to the reaction zone 704a from a reservoir on the device, e.g., well 706e, or from a source external to the device (not shown). The test compound is then screened for an effect on the reaction of interest.

Optionally, the devices are configured to operate in a high-throughput screening format, e.g., as described in U.S. Pat. No. 5,942,443. In particular, instead of delivering potential test compounds to the reaction zone from a reservoir integrated into the body of the device, such test compounds are introduced into the reaction zone via an external sampling pipettor or capillary that is attached to the body of the device and fluidly coupled to the reaction zone. Such pipettor systems are described in, e.g., U.S. Pat. No. 5,779,868. The sampling Pipettor is serially dipped into different sources of test compounds which are separately and serially brought into the reaction zone to ascertain their effect, if any, on the reaction of interest.

Movement of materials through the channels of these microfluidic channel networks is typically carried out using any of a variety of known techniques, including electrokinetic material movement (e.g., as described in U.S. Pat. No. , 5,858,195, pressure based flow, axial flow or rotor systems, gravity flow, or hybrids of any of these.

EXAMPLES

Example 1

A Homogeneous Kinase Assay Based Upon Thiophosphorylation and Biotinylation

A. Thiophosphorylation of Kemptide

A typical reaction mixture (50 µl) contained 20 mM HEPES pH 7.5, 10 mM $MgCl_2$, 50 µM fluorescein labeled Kemptide (Research Genetics, Huntsville, Ala., USA), 500 µM ATPγS (Sigma, St. Louis, Mo., USA, #A-1388), and 1 µl of the catalytic subunit of cAMP dependent protein kinase A (Promega Corp., Madison, Wis., USA, #V5161). The approximate final concentration of the enzyme was 700 nM. In inhibition experiments, the PKA inhibitor H-89 (Calbiochem, San Diego, Calif., USA, #371963) was added to the reaction mixture at the concentrations indicated below. The mixture was incubated at room temperature for 15 min and the reaction terminated by the addition of EDTA to 45 mM. As a negative control, EDTA was added to one of the reaction mixtures before the addition of the kinase. The extent of thiophosphorylation was then analyzed by capillary electrophoresis with fluorescence detection either on a Beckman P/ACE System 5500 instrument, using a 50 µm fused silica capillary with 50 mM borate, pH 8.6 as the separation buffer, or on a microfabricated chip as described in Cohen et al., Anal. Chem. 273:89–97 (1999). Substrate and product peak areas were integrated and the extent of substrate phosphorylation was determined from their ratio.

B. Biotinylation of the thiophosphorylated product

To 45 µl of the thiophosphorylation mixture was added 5 µl of a freshly prepared 10 mM solution of iodoacetyl-LC-biotin (Pierce, Rockford, Ill., #21333) in DMSO. The mixture was left at room temperature overnight, protected from light. The outcome of the biotinylation reaction could be determined at this point by capillary electrophoresis as described above, however, this is not required, nor is it preferred.

C. Fluorescence Polarization Measurements Polarization measurements were carried out on a FluoroMax-2 (Instruments S. A., Edison, N.J.) using excitation at 490 nm and emission at 525 nm. An aliquot (1 µl) of the biotinylation reaction from step B was diluted in 400 µl of 50 mM HEPES, pH 7.4 and its fluorescence polarization measured. Four µl of a 160 µM solution of streptavidin were then added to this solution and the polarization measured again. In preliminary streptavidin titration experiments we established that this amount of streptavidin was sufficient to generate a maximal fluorescence polarization signal; the addition of more streptavidin did not increase that signal further.

D. Calculations

To quantitate the extent of Kemptide phosphorylation from the measured fluorescence polarization values, the following equation was used (see, e.g., Lundblad et al., Molec. Endocrinol. 10:607–612):

$$c_{prod} = (F_{obs} - F_{sub}) / \{(F_{prod} - F_{obs})R + F_{obs} - F_{sub}\}$$

where $c_{prod}$ is the molar fraction of the thiophosphorylated, biotinylated product; $F_{sub}$, $F_{prod}$ and $F_{obs}$ are the experimentally measured fluorescence polarization values in the presence of streptavidin for the pure substrate (1), pure product (4) and the mixture thereof, respectively; and R is the ratio of the quantum yields of the fluorescein tag in the two molecules, 4 and 1, in the presence of streptavidin. The values of $F_{sub}$ and $F_{prod}$ were determined from samples that contained pure Kemptide 1 and pure thiophosphorylated, biotinylated Kemptide 4, in the presence of excess streptavidin. The value of R was determined by measuring the fluorescence polarization of an equimolar mixture of these two compounds (i.e., $c_p$=0.5) and solving the equation for R.

E. Results

Figure 4:
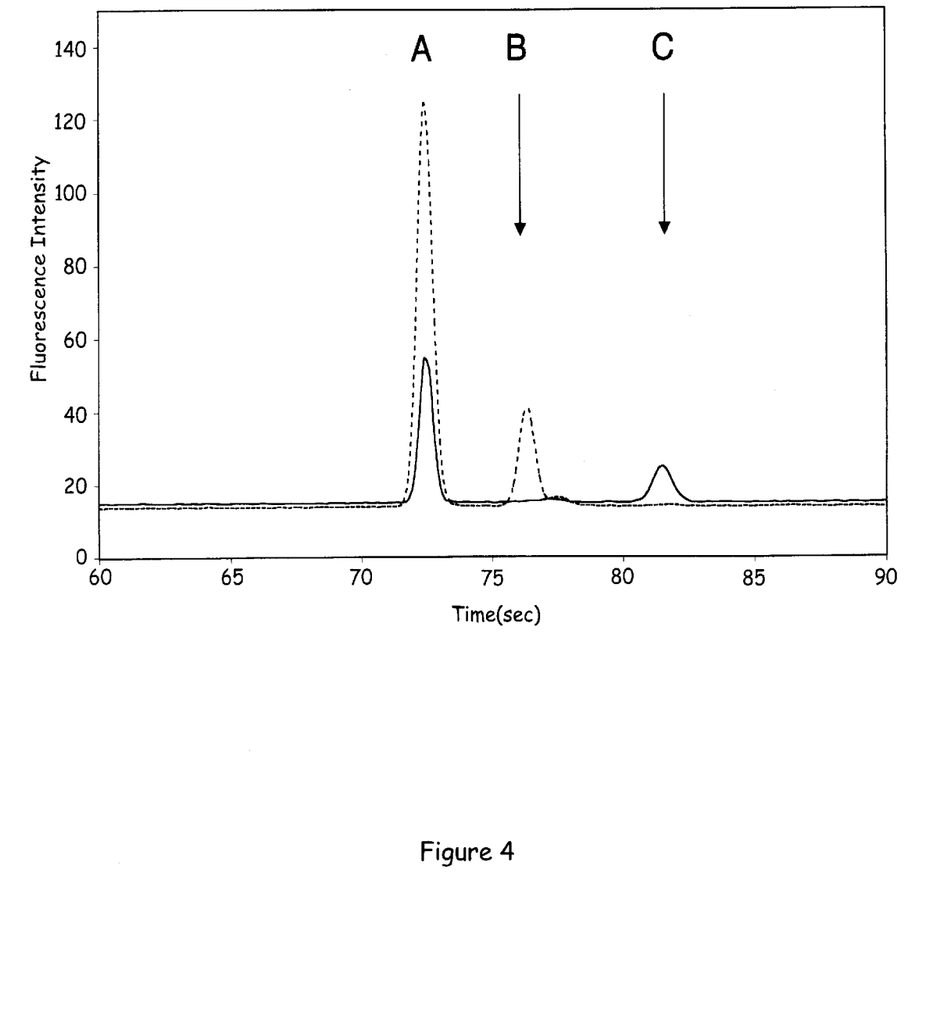
FIG. 4 illustrates overlaid electropherograms of a mixture of PKA substrate (peak A) and its thiophosphorylated derivative (peak C) before (solid line) and after (dotted line) treatment with the iodoacetyl-LC-biotin. The thiophosphorylated derivative is quantitatively biotinylated (peak B).

FIG. 4 shows the overlaid electropherograms of a mixture containing approximately 80% of Kemptide 1 and 20% of its thiophosphorylated derivative 2 before and after the treatment with the iodoacetamide derivative of biotin 3. Peak A in both electropherograms is the starting fluorescein labeled Kemptide, peak B is the thiophosphorylated, biotinylated product 4, and peak C is the product of the PKA catalyzed reaction, compound 2. As expected, the treatment of the mixture of compounds 1 and 2 with the sulfur-specific reagent 2 led to the quantitative biotinylation of the thiophosphate 2 while compound 1 remained unchanged.

The effect of streptavidin addition on the fluorescence polarization values of two solutions containing either pure Kemptide 1 or pure biotinylated thiophosphate 4 was then studied. These two solutions were obtained by PKA catalyzed thiophosphorylation reactions in the presence or absence of EDTA, followed by treatment with iodoacetyl-LC-biotin. The presence of EDTA was expected to completely inhibit the phosphorylation reaction by chelating the $Mg^{2+}$; the composition of the two solutions was confirmed by capillary electrophoresis. The fluorescence polarization value for both solutions in the absence of streptavidin was found to be 38–40 milliP (P=polarization unit). The addition of increasing concentrations of streptavidin resulted in increasing polarization values for the solution of compound 4, until a maximum signal of 180–185 mP was reached; no change in the fluorescence polarization signal was observed for compound 1. We found these values to be highly reproducible, but since fluorescence polarization is sensitive to temperature, it is advisable to experimentally measure these two values with every set of kinase reactions.

Figure 5:
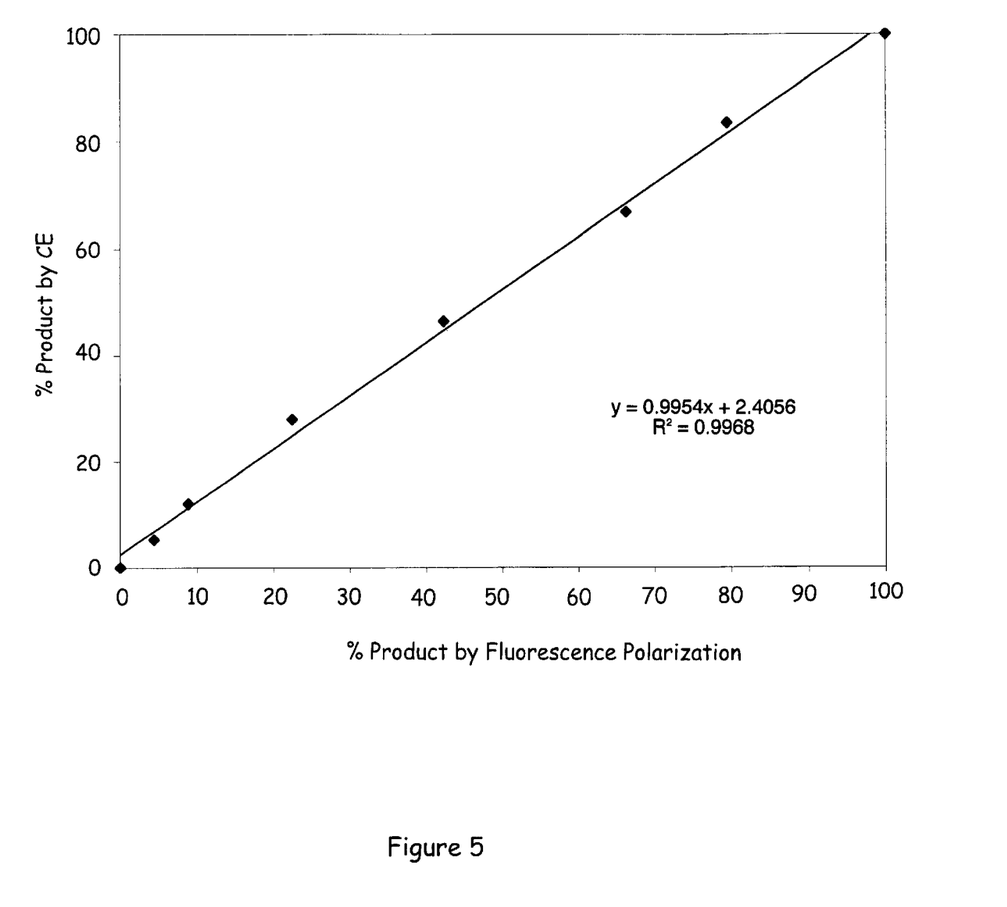
FIG. 5 illustrates the correlation between capillary electrophoretic separation and detection and fluorescence polarization detection in analyzing the PKA reactions.

By mixing aliquots of pure compounds 1 and 2 in different proportions, several solutions were prepared representing kinase reaction products with various degrees of substrate conversion. The exact composition of these mixtures was determined by capillary electrophoresis. The same mixtures were then treated with iodoacetyl-LC-biotin and finally their composition was analyzed by measurements of their fluorescence polarization signals in the presence of streptavidin. From these values, the exact composition was calculated as described in the Experimental section. The quantitation results from both analytical methods, capillary electrophoresis and fluorescence polarization in the presence of streptavidin, showed excellent agreement as demonstrated in FIG. 5.

Figure 6:
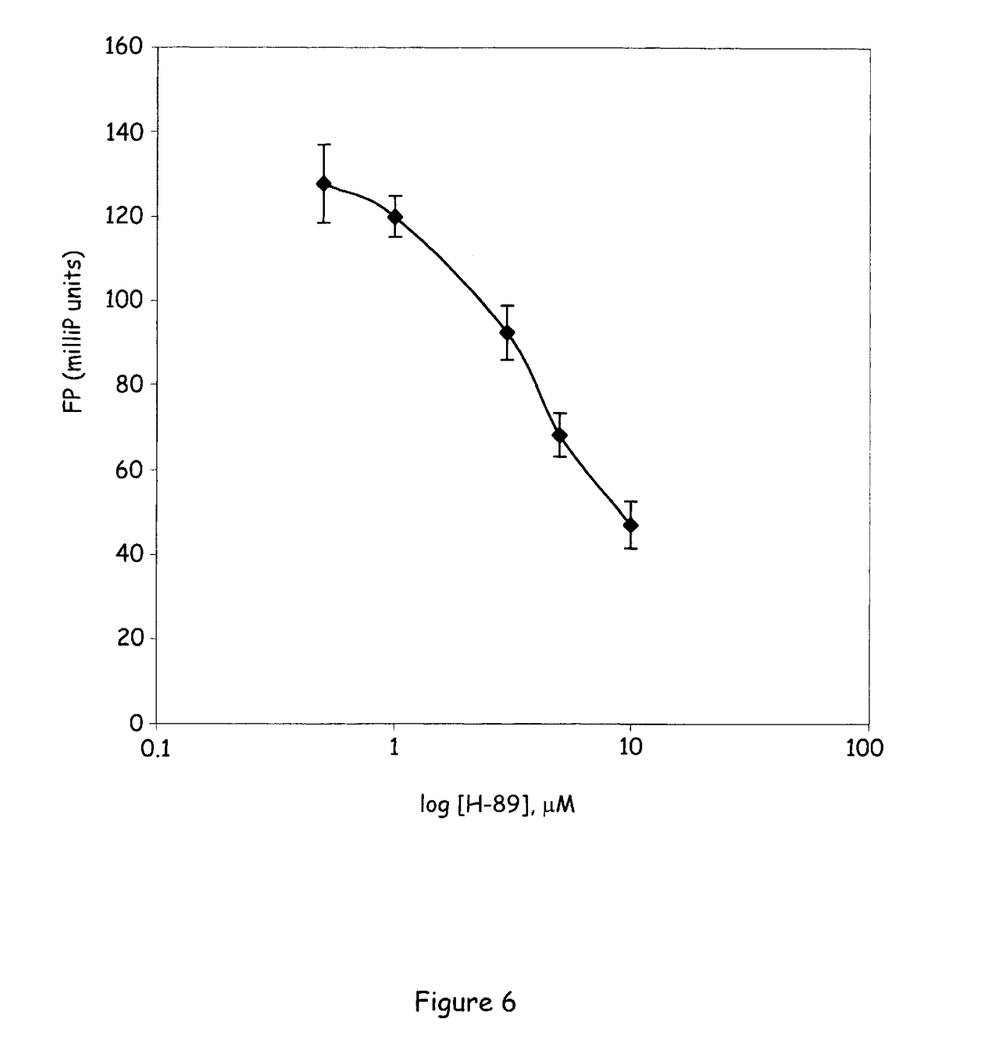
FIG. 6 illustrates PKA inhibition by H-89 as determined by fluorescence polarization measurements in the presence of streptavidin following thiophosphorylation and biotinylation reactions.

The suitability of this approach for the detection of kinase inhibitors was then tested by performing PKA reactions in the presence of a range of concentrations (0.5–10 µM) of compound H-89, an ATP competitive PKA inhibitor. Following a 15-min incubation, the reactions were stopped by the addition of EDTA, treated with iodoacetyl-LC-biotin, and analyzed by fluorescence polarization in the presence of streptavidin. Triplicate measurements of each sample were carried out, the average polarization values and standard deviations for all samples are shown in FIG. 6. From the observed polarization signals the substrate conversion was calculated as described above, and an $IC_{50}$ value of approximately 5 μM was estimated for this inhibitor under the experimental conditions used. Since $IC_{50}=K_i(1+[S]/K_m)$, where [S] is the ATPγS concentration and $K_m$ is the Michaelis-Menten constant for this co-factor, we calculated a $K_i$ value of about 60 nM (the ATPγS concentration used was 500 μM; the $K_m$ value was determined to be about 6 μM by running PKA assays at different ATPμS concentrations on a microchip as recently described in Cohen et al., supra. This $K_i$ value is in very good agreement with the previously reported inhibitory constant of 48 nM for this compound. See, e.g., Chijiwa et al., J. Biol. Chem. 265:5267–5272.

Unless otherwise specifically noted, all concentration values provided herein refer to the concentration of a given component as that component was added to a mixture or solution independent of any conversion, dissociation, reaction of that component to a alter the component or transform that component into one or more different species once added to the mixture or solution.

All publications and patent applications are herein incorporated by reference to the same extent as if each individual publication or patent application was specifically and individually indicated to be incorporated by reference. Although the present invention has been described in some detail by way of illustration and example for purposes of clarity and understanding, it will be apparent that certain changes and modifications may be practiced within the scope of the appended claims.

2. The method of claim 1, wherein the reactant bears a haloacetate group.

3. The method of claim 2, wherein the haloacetate group consists of an iodoacetyl group.

4. The method of claim 2, wherein the haloacetate group consists of a bromoacetyl group.

5. The method of claim 1, wherein the protein consists of streptavidin.

6. The method of claim 1, wherein:
   the reactant comprises biotin that is incorporated into the second product; and
   the detecting step comprises adding streptavidin to the second product, and measuring a difference in a fluorescence polarization level from the second product as compared to a fluorescence polarization of the peptide substrate.

7. The method of claim 1, wherein the contacting steps are carried out in at least a first channel of a microfluidic device.

8. The method of claim 5, wherein the contacting steps are carried out in at least a first channel of a microfluidic device.

9. The method of claim 6, wherein the contacting steps are carried out in at least a first channel of a microfluidic device.

10. The method of claim 1 wherein the protein consists of avidin.

11. The method of claim 1 wherein the reactant consists of biotin.

12. The method of claim 1 wherein the biotin derivative consists of iodoacetyl-LC-biotin.

13. A method of identifying a phosphorylatable substrate for a kinase enzyme, comprising:

---

---

We claim:

1. A method of assaying a kinase-mediated coupling reaction between a flourescently labeled phosphorylatable peptide substrate and a thiol derivative, comprising:
   contacting the fluorescently labeled phosphorylatable peptide substrate with the thiol derivative in the presence of the kinase to yield a first product comprising a thiophosphate group;
   contacting the first product with a reactant that comprises a thiol-reactive biotin derivative to yield a second product;
   contacting the second product with a biotin-binding protein; and
   detecting a difference in a fluorescence polarization level from the second product as compared to a fluorescence polarization of the peptide substrate, to assay the kinase mediated coupling reaction between the peptide substrate and the thiol derivative.

providing a phage display peptide library wherein each peptide in the library comprises a conserved phosphorylatable amino acid residue;
reacting the phage display library with the kinase and ATPγS;
contacting the phage display library with a biotinylated haloacetate following the reacting step;
immobilizing any biotinylated phage from the contacting step on a solid support;
isolating and sequencing DNA from any phage immobilized on the solid support in the immobilizing step; and
determining a phosphorylatable peptide sequence from a sequence of the DNA isolated from the phage.

14. A method of assaying a kinase-mediated coupling reaction between a fluorescently labeled phosphorylatable peptide substrate and a phosphorylated thiol derivative comprising:
   contacting the fluorescently labeled phosphorylatable peptide substrate with the phosphorylated thiol derivative in the presence of the kinase to yield a first product comprising a thiophosphate group;

contacting the first product with a thiol-reactive biotin derivative to yield a second product;

contacting the second product with a biotin-binding protein; and detecting a difference in a fluorescence polarization level from the second product as compared to a fluorescence polarization of the peptide substrate to assay the kinase mediated coupling reaction between the peptide substrate and the phosphorylated thiol derivative.

15. The method of claim 14 wherein the protein consists of streptavidin.

16. The method of claim 14 wherein the protein consists of avidin.

17. The method of claim 14 wherein the protein is of sufficiently large molecular weight to give the second product a distinguishable fluorescence polarization from the peptide substrate.

18. The method of claim 14 wherein the biotin derivative consists of iodoacetyl-LC-biotin.

* * * * *